United States Patent
Frigg

(10) Patent No.: US 9,326,800 B2
(45) Date of Patent: May 3, 2016

(54) DEVICE FOR THE CEMENT AUGMENTATION OF BONE IMPLANTS

(75) Inventor: Robert Frigg, Bettach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 232 days.

(21) Appl. No.: 11/817,376

(22) PCT Filed: Mar. 24, 2005

(86) PCT No.: PCT/CH2005/000173
§ 371 (c)(1),
(2), (4) Date: Dec. 14, 2007

(87) PCT Pub. No.: WO2006/099751
PCT Pub. Date: Sep. 28, 2006

(65) Prior Publication Data
US 2008/0119945 A1    May 22, 2008

(51) Int. Cl.
*A61F 2/28* (2006.01)
*A61B 17/70* (2006.01)
*A61B 17/68* (2006.01)
(Continued)

(52) U.S. Cl.
CPC .......... *A61B 17/7098* (2013.01); *A61B 17/686* (2013.01); *A61B 17/8805* (2013.01); *A61B 17/8808* (2013.01); *A61F 2/30723* (2013.01); *A61F 2/30724* (2013.01); *A61F 2/30907* (2013.01); *A61F 2/4601* (2013.01); *A61F 2/4614* (2013.01); *A61F 2002/30011* (2013.01); *A61F 2002/30042* (2013.01); *A61F 2002/3068* (2013.01); *A61F 2002/30115* (2013.01); *A61F 2002/30224* (2013.01); *A61F 2002/30405* (2013.01); *A61F 2002/30583* (2013.01); *A61F 2002/30919* (2013.01); *A61F 2002/4475* (2013.01); *A61F 2002/4631* (2013.01); *A61F 2220/0025* (2013.01); *A61F 2220/0041* (2013.01); *A61F 2230/0069* (2013.01);
(Continued)

(58) Field of Classification Search
None
See application file for complete search history.

(56) References Cited

U.S. PATENT DOCUMENTS 4,439,152 A * 3/1984 Small ............................ 433/173
4,671,768 A * 6/1987 Ton ............................... 433/174
(Continued)

FOREIGN PATENT DOCUMENTS

DE    35 08 759 A1    10/1985
DE    29501042         3/1995
(Continued)

OTHER PUBLICATIONS

International Search Report for International Application No. PCT/CH05/00173. mailed Dec. 1, 2005.
(Continued)

*Primary Examiner* — Yashita Sharma
*Assistant Examiner* — Rebecca Preston
(74) *Attorney, Agent, or Firm* — Wayne C. Jaeschke, Jr.

(57) ABSTRACT

A device for cement augmentation of bone implants that includes a hollow cylinder having an inner diameter, an outer diameter and a longitudinal axis. The hollow cylinder includes an inner cavity, a front end configured and adapted for insertion into a bone, a rear end having a bore hole in communication with the inner cavity, and a shell having at least one perforation. The device also includes a bone implant insertable into the hollow cylinder. The hollow cylinder is adapted and configured to receive unhardened bone cement through the bore hole into the inner cavity.

21 Claims, 2 Drawing Sheets

(51) Int. Cl.

| | |
|---|---|
| A61B 17/88 | (2006.01) |
| A61F 2/30 | (2006.01) |
| A61F 2/46 | (2006.01) |
| A61F 2/44 | (2006.01) |

(52) U.S. Cl.
CPC ............. *A61F2310/00011* (2013.01); *A61F 2310/00353* (2013.01)

(56) References Cited

U.S. PATENT DOCUMENTS

| | | | |
|---|---|---|---|
| 5,169,400 A | 12/1992 | Mühling et al. | |
| 5,571,139 A | 11/1996 | Jenkins | |
| 5,755,720 A | 5/1998 | Mikhail et al. | |
| 5,890,902 A * | 4/1999 | Sapian | 433/173 |
| 5,902,303 A | 5/1999 | Eckhof et al. | |
| 6,059,829 A * | 5/2000 | Schlapfer et al. | 623/17.16 |
| 6,168,597 B1 | 1/2001 | Biedermann et al. | |
| 6,383,190 B1 | 5/2002 | Preissman | |
| 6,454,769 B2 | 9/2002 | Wagner et al. | |
| 6,605,089 B1 * | 8/2003 | Michelson | 606/32 |
| 6,679,890 B2 * | 1/2004 | Margulies et al. | 606/94 |
| 6,896,462 B2 * | 5/2005 | Stevenson et al. | 411/82 |
| 7,338,493 B1 * | 3/2008 | Vandewalle | 606/86 A |
| 7,708,738 B2 | 5/2010 | Fourcault et al. | |
| 2001/0039457 A1 * | 11/2001 | Boyer et al. | 623/23.52 |
| 2003/0105468 A1 * | 6/2003 | Gorek | 606/92 |
| 2003/0224328 A1 * | 12/2003 | Sapian | 433/173 |
| 2004/0225292 A1 * | 11/2004 | Sasso et al. | 606/73 |
| 2004/0243130 A1 * | 12/2004 | Biscup | 606/73 |
| 2005/0070900 A1 * | 3/2005 | Serhan et al. | 606/61 |
| 2006/0025773 A1 | 2/2006 | Yevmenenko et al. | |
| 2008/0269768 A1 | 10/2008 | Schwager et al. | |
| 2009/0187194 A1 | 7/2009 | Hamada | |
| 2010/0069970 A1 | 3/2010 | Lewis et al. | |

FOREIGN PATENT DOCUMENTS

| | | |
|---|---|---|
| DE | 2 5 01 042 U1 | 5/1995 |
| DE | 196 05 735 A1 | 6/1995 |
| DE | 200 09 626 | 8/2000 |
| EP | 2 140 824 | 1/2010 |
| JP | 03-085179 | 4/1991 |
| JP | 04-221538 | 8/1992 |
| JP | 07-313586 | 12/1995 |
| JP | 08-024347 | 1/1996 |
| JP | 09-201330 | 8/1997 |
| JP | 11-504552 A | 4/1999 |
| JP | 2003 159258 | 6/2003 |
| WO | WO 90/08510 | 8/1990 |
| WO | WO-01/32100 A2 | 5/2001 |
| WO | WO 2004/098425 | 11/2004 |
| WO | WO-2006/099751 A1 | 9/2006 |
| WO | WO 2010/093658 | 8/2010 |

OTHER PUBLICATIONS

"European Patent Application No. 04750971.6, Communication mailed Jun. 12, 2008", 5 pgs.

"International Application Serial No. PCT/CH2005/000173, International Search Report mailed Dec. 1, 2005", 4 pgs.

"International Application Serial No. PCT/CH2005/000173, Written Opinion mailed Dec. 1, 2005", 6 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels that Support Tissue Formation in Vitro", *Macromolecules*, 32, (1999),7370-7379.

International Patent Application No. PCT/US2010/023703: Written Opinion of the International Preliminary Examining Authority dated Apr. 18, 2011, 7 pages.

* cited by examiner

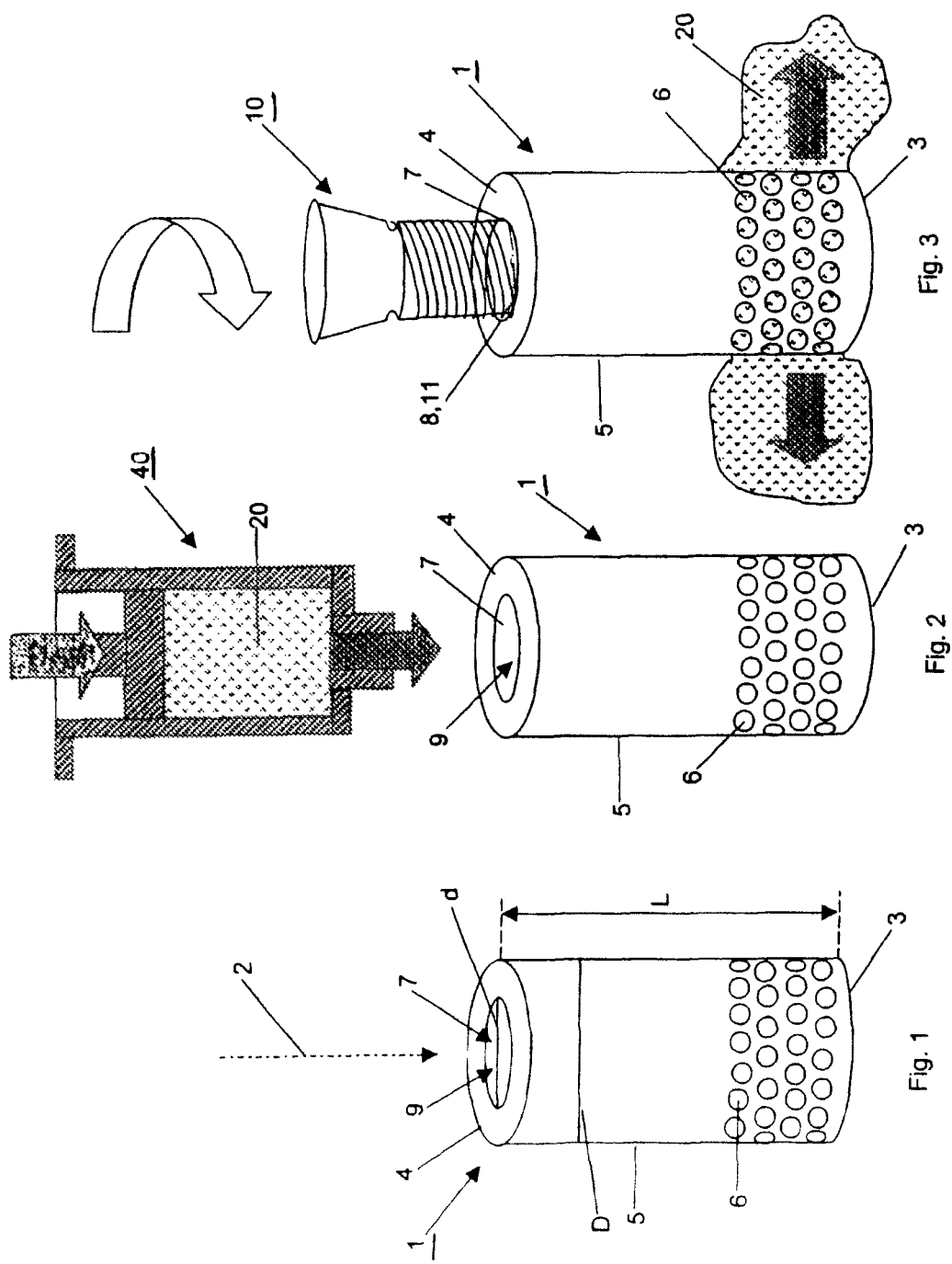

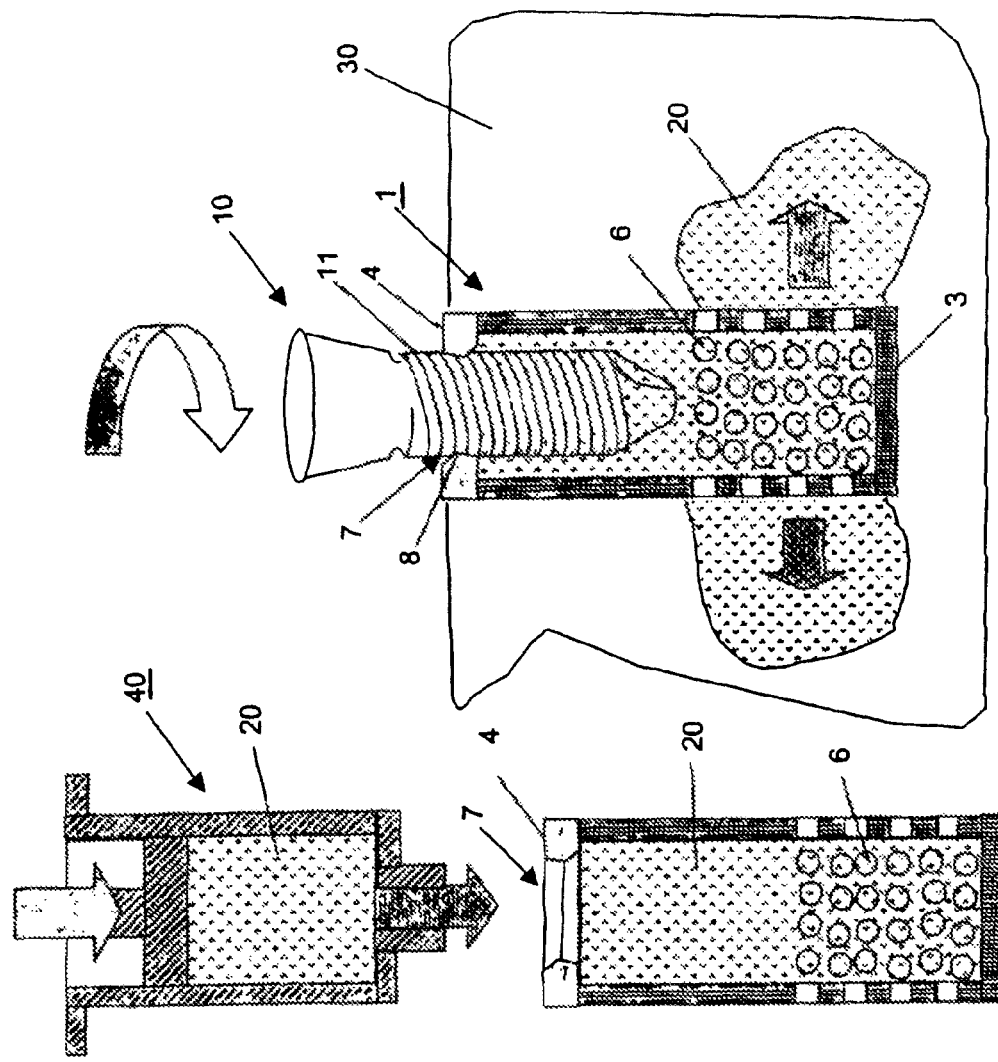
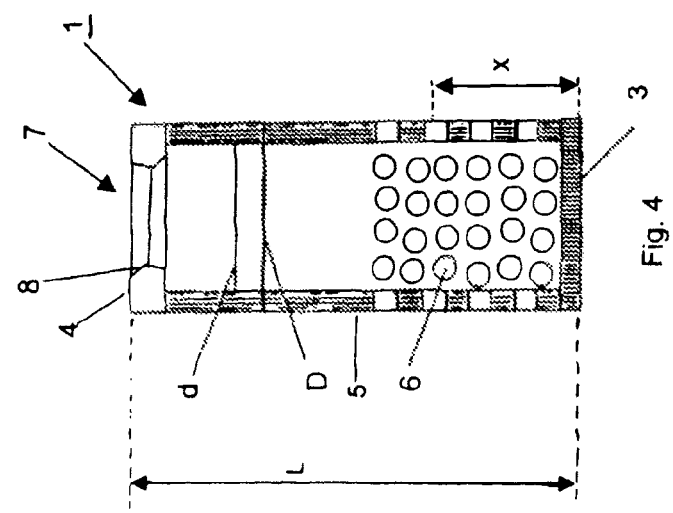

DEVICE FOR THE CEMENT AUGMENTATION OF BONE IMPLANTS

CROSS-REFERENCE TO RELATED APPLICATIONS

This application is a national stage application of International Application No. PCT/CH2005/000173, filed Mar. 24, 2005, the entire contents of which are incorporated herein by reference.

BACKGROUND OF THE INVENTION

1. Field of the Invention

Embodiments of the present invention relate to a device for the cement augmentation of bone implants.

2. Description of the Related Art

Bone cement augmentation in bone surgery has been known for several years. This augmentation is applied in osteoporotic bones where bone anchoring means such as screws, pins, nails and so on, may not anchor rigidly.

According to the known technology, the bone cement is inserted into the bone and is suitable as an anchoring bed for subsequently inserted implants. With bone cement, every bone filling material is understood to be hardenable by means of polymer, hydraulic or according to other reaction mechanisms. These implants are inserted before the cement hardens such that the cement may add on adhere to and anchor the implants. The drawback of this known technology is the complicated application of the bone cement and the difficulty in determining the correct position of the implant within the cement composite.

In order to solve these problems, particular implants have been developed that allow an application of the cement after the implant is inserted into the bone. Typically, implants and, particularly screws, have been used which that comprise a cannulation wherethrough the cement may be filled into the bone. This technology, however, requires a high viscous cement that may be injected through the relatively small cannulation. Furthermore, the amount and the position of the cement in the bone may not be controlled sufficiently. Bone cements having a lower viscosity, which have significant biological advantages with regard to bone cements that are not resorbable and that harden at a high temperature, are not suitable for use with these adapted implants.

From DE-A-3 508 759 to TRONZO, for example, a hip screw is known that is provided with a central through bore, said through bore opening in an open screw tip and having sideward openings between the thread walls. By means of this hip screw, anchoring of the oversized and pointed thread in the bone can be achieved on the one side hand, and on the other side hand a strengthening of the weakened bone material can be achieved by means of injecting the bone cements through the central bore, allowing the bone cement to flow through the sideward openings. The main disadvantage of this technology is that no common bone implants may not be used but instead specially manufactured, costly and complicated implants (hip screw) are necessary.

On this point, embodiments of the present invention intend to remedy the disadvantages of the known technology. Embodiments of the present invention are based on the objective of providing a device by means of which the cement augmentation of existing and/or novel bone anchoring means (or other bone implants) may be simplified.

SUMMARY OF THE INVENTION

The invention solves the known problems with a device for cement augmentation of bone implants that includes a hollow cylinder having an inner diameter, an outer diameter and a longitudinal axis. The hollow cylinder comprises an inner cavity, a front end configured and adapted for insertion into a bone, a rear end having a bore hole in communication with the inner cavity, and a shell having at least one perforation. The device also includes a bone implant insertable into the hollow cylinder. The hollow cylinder is adapted and configured to receive unhardened bone cement through the bore hole into the inner cavity.

The device according to embodiments of the present invention separates the particular augmentation from the implant that is to be augmented, whereby the intra-operative handling is simplified and securement of this treatment technology is increased.

With the instant invention, a perforated hollow cylinder, pre-filled with bone cement, is inserted into a bone. Depending on the situation, the seat for the hollow cylinder in the bone may have to be prepared. This may be achieved through boring and/or reaming. After the hollow cylinder has been seated, the bone implant (e.g. bone screw, blade, spiral blade, bone nail) corresponding to the hollow cylinder is inserted into the hollow cylinder thereby displacing the cement through the perforations in the hollow cylinder in and into the surrounding bone. The amount of displaced cement equals the volume of the anchoring means inserted into the hollow cylinder. Depending on the position and number of perforations in the hollow cylinder, the augmentation may be achieved in a desired region. Because of the separation of the augmentation device from the implant, a cement augmentation may be achieved using usual available commercial implants.

With the present invention, application of the cement is not directly into the bone, as is the case with known augmentation techniques but instead is directed into the hollow cylinder on the operating table. The hollow cylinder may be inserted in the prepared seat in the bone after filling has been completed.

Basically, the hollow cylinder may be applied in every situation where the bone material does not give enough rigidity for common anchoring means, for example, in the regions near a bone joint, the vertebra, jawbone, pelvis and so on.

The advantages achieved by the embodiments of the present invention are as follows:

application of the cement exterior of the body results in:
  i) simple handling of the cement;
  ii) a controllable and doseable filling procedure;
  iii) there is no inclusion of blood, liquid and tissue in the cement;

through orientation, positioning, number and dimensioning of the perforations, the cement is delivered to the anatomically desired location;

the amount of cement emerging from the hollow cylinder may be controlled via the volume of the bone anchoring element; and the risk of uncontrolled loss of a large amount of cement in the fracture region because of non-controllable decrease of resistance (spontaneous bone fracture in the treatment area) is prevented because the emerging amount of cement is controlled via the insertion of the implant and not via an applied pressure against the resistance of the bone.

In one embodiment of the present invention, the hollow cylinder is at least partially filled with unhardened bone cement.

In another embodiment of the present invention, the hollow cylinder and the bone anchoring element are mutually adapted such that upon insertion of the bone anchoring element into the hollow cylinder, the unhardened bone cement flows out through the at least one perforation in the shell of the hollow cylinder.

In a further embodiment of the present invention, the hollow cylinder is closed at its front end. The advantage achieved therewith is that the cement flows out only sidewardly where it is most suitable as a hardened cluster of cement in front of the hollow cylinder may be disadvantageous because upon further screwing in of the bone implant, the cluster of cement might penetrate into the corticalis in front of it. For example, in TRONZO, the bone anchoring element may not be screwed in an axial direction towards the front after hardening of the cement, because, after hardening, the cement displaced through the open tip does not allow this. An additional advantage of the hollow cylinder being closed at its front end is achieved when it is applied near a bone joint.

In yet another embodiment of the present invention, the rear end of the hollow cylinder is configured as a coupling for connection with a syringe containing the bone cement. Specifically, the rear end of the hollow cylinder may have a plug-in connection for an adapter for coupling with the syringe containing the bone cement. This impermeable connection prevents, on the one hand, a loss of pressure, and on the other hand, an undesired overflow of bone cement at the rear end of the hollow cylinder.

In still a further embodiment of the present invention, the rear end of the hollow cylinder is configured with a bore hole having an interior thread. Thus, the bone implant may be configured as a bone screw with an exterior thread matching the interior thread of the hollow cylinder.

In still another embodiment of the present invention, the rear end of the hollow cylinder is provided with an aperture having the same cross-section as the bone implant, e.g. in the form of a screw thread or slot for a blade.

In a further embodiment of the present invention, the hollow cylinder has a total length L and the perforations are located at a maximum distance L/2, preferably L/3, from the front end. In this configuration, bone cement flows out only in the frontal region of the hollow cylinder where it is most advantageous. The flowing out of bone cement at the rear portion is medically rather disadvantageous.

In another embodiment of the present invention, the rear end of the hollow cylinder is configured to have a cavity with a polygonal cross-section or TORX-cavity, which permits insertion of a respective polygonal- or TORX screw driver.

The diameter of perforations is typically in the range between 0.9 mm and 3.3 mm, and preferably in the range between 1.5 mm and 2.5 mm. The number of perforations is typically at least 20, preferably at least 40. The maximum number of perforations is typically maximum 100, preferably maximum 60. Preferably, the ratio D/F between the outer diameter of the hollow cylinder in mm and the total outflow area F of the perforations in $mm^2$ is in the range between 0.19 and 0.36 $mm^{-1}$ The wall thickness (outer diameter D minus inner diameter d) of the hollow cylinder is preferably in the range between 0.1 and 2.0 mm.

Common implant materials such as steel or titanium are suitable, but synthetics such as PEEK or resorbable or non-resorbable polymers, may be used as well. The hollow cylinder may manufactured of a mesh, a braiding or a fully or partially perforated tube. By means of the position, diameter and number of perforations the outflow of cement may be controlled with respect to location and amount and may be adjusted based on the cement being used.

The face of the front end may be open or closed depending on the requirements. The closed embodiment prevents a facial outflow of the cement, which is important for some applications (application near a bone joint).

Additional advantageous embodiments of the present invention are characterized in the subclaims.

Embodiments of the present invention and additional configurations of the invention are explained in more detail with reference to the partially schematic illustrations of several embodiments.

BRIEF DESCRIPTION OF THE DRAWINGS

FIG. 1 is a front perspective view of a hollow cylinder for the device, according to an embodiment of the present invention;

FIG. 2 is a front perspective view of the hollow cylinder according to FIG. 1 with a longitudinal section through a cement syringe for pressing the bone cement in the hollow cylinder;

FIG. 3 is a front perspective view of the hollow cylinder according to FIG. 1 filled with bone cement whereby a bone screw is inserted, thereby pressing a portion of the bone cement out of the hollow cylinder into the surrounding bone;

FIG. 4 is a longitudinal cross-section through the empty hollow cylinder according to FIG. 1;

FIG. 5 is a longitudinal cross-section through the hollow cylinder and bone cement syringe according to FIG. 2, filled with bone cement; and FIG. 6 is a longitudinal cross-section through the hollow cylinder according to FIG. 3 filled with bone cement and having a bone screw inserted into the hollow cylinder thereby pressing a portion of the bone cement out of the hollow cylinder into the surrounding bone.

DESCRIPTION

The embodiment of the present invention shown in FIG. 1 comprises a hollow cylinder 1 with a front end 3, a rear end 4 and a longitudinal axis 2. The hollow cylinder 1 has a total length L extending parallel to the longitudinal axis 2 and an outer diameter D measured orthogonally to the longitudinal axis 2. The cavity 9 of the hollow cylinder 1 has an inner diameter d measured orthogonally to the longitudinal axis 2. The cavity 9 of the hollow cylinder 1 is enclosed by a shell 5 along the total length L, whereby the shell 5 is partially provided with perforations 6. Examples of perforations include holes or a mesh grid. The total area of all perforations 6 sums up to a total outlet area F, which is smaller than the surface area of the shell 5.

The front end 3 of the hollow cylinder 1 may be open or closed with the closed embodiment being advantageous because the formation of cement clusters in front of the hollow cylinder 1 may be prevented. At its rear end 4, the hollow cylinder 1 is provided with a bore hole 7 opening into the cavity 9 such that it serves as inlet for bone cement. In a further embodiment, the bore hole 7 may be provided with an interior thread 8 (FIG. 3).

The embodiment of the present invention shown in FIG. 2 comprises a hollow cylinder 1 having a shell 5 that is provided with perforations 6, a front end 3 and a rear end 4. A bore hole 7 penetrates the hollow cylinder 1 through to the front end 3, said bore hole 7 being adapted to receive the bone cement 20 from a cement syringe 40 (longitudinal section) into the cavity 9 of the hollow cylinder 1.

FIG. 3 comprises a hollow cylinder 1 filled with bone cement 20 and has a closed front end 3. At the rear end 4, the bore hole 7 is provided with an interior thread 8 in the hollow cylinder 1. The bone implant 10 here is configured as a bone screw. The interior thread 8 matches the exterior thread of the bone screw such that the bone screw is screwable into the hollow cylinder 1. Because the shell 5 is provided with perforations 6, a portion of the bone cement 20 is pressed radially outward through the perforations 6 and out of the hollow cylinder 1 by means of the bone screw.

The embodiment of the present invention shown in FIG. 4 depicts a longitudinal section through the empty hollow cylinder 1 according to FIG. 1, whereby the front end 3 of the hollow cylinder 1 is closed and the bore hole 7 is provided with an interior thread 8 at the rear end 4. The hollow cylinder 1 has an outer diameter D and an inner diameter d. The shell 5 of the hollow cylinder 1 is provided with perforations 6 over a partial length of the shell, where X<L measured from the front end 3.

FIG. 5 shows a longitudinal section through a hollow cylinder 1 filled with bone cement 20 and having a closed front end 3 as well as a bore hole 7 at the rear end 4. Furthermore, FIG. 5 depicts a longitudinal section through a bone cement syringe 40 filled with bone cement 20.

FIG. 6 depicts a longitudinal section through the hollow cylinder 1 filled with bone cement 20 shown in FIG. 3, said hollow cylinder 1 having a closed front end 3 and a rear end 4 provided with a bore hole 7. A bone implant 10 is inserted into the bore hole 7 at the rear end 4, said bone implant 10 being provided with a exterior thread 11 that matches with the interior thread 8 in the bore hole 7. By means of inserting the bone implant 10, the bone cement 20 is pressed out of the hollow cylinder 1, through the perforations 6 and into the surrounding bone 30.

The surgical technique for implanting the bone implant according to the embodiments of the present invention is described as follows:
  a) the seat for the hollow cylinder is prepared in the bone by means of, for example, reaming the bone;
  b) a hollow cylinder is chosen based on its length and diameter and is filled with bone cement in a common manner outside of the patient's body;
  c) in order to prevent an outflow of the bone cement through the perforations in the cylinder shell, the hollow cylinder may, for example, be inserted into a sleeve having a corresponding bore;
  d) the pre-filled hollow cylinder is then inserted in the bone; and
  e) the bone implant (e.g. a bone screw) is inserted into the hollow cylinder through the rear end of the hollow cylinder. During this procedure, the bone cement is pressed through the perforations, out of the hollow cylinder into the bone structure surrounding the hollow cylinder.

After the bone cement has hardened, the bone cement generates a unit comprising the bone, the hollow cylinder and the bone implant.

The invention claimed is:

1. A device for cement augmentation of the bone implants, the device comprising:
  a hollow cylinder including a shell and defining a closed front end configured to be inserted into bone, an opposed open rear end that includes an inner surface defining a bore hole, and an inner cavity that is in communication with the bore hole, the shell defining a plurality of perforations that extend through the shell in communication with the inner cavity;
  a bone implant having a length so as to define a proximal end and an opposed distal end, the bone implant having an exterior thread that extends from the distal end toward the proximal end along a portion of the length, the exterior thread of the bone implant configured to mate with the inner surface of the hollow cylinder to thereby advance the portion of the bone implant having the exterior thread into the hollow cylinder as the bone implant is rotated with respect to the hollow cylinder; and
  unhardened bone cement
  wherein (i) the hollow cylinder received the unhardened bone cement in the inner cavity, and (ii) the length of the bone implant is sufficient to extend within a majority of the cavity such that the distal end of the bone implant presses against the bone cement as the bone implant advances into the hollow cylinder, and the perforations are sized such that the pressed bone cement is driven through the perforations, wherein the hollow cylinder has a length and the perforations have a maximum distance to the front end of the shell that is equal to approximately the length of the hollow cylinder/2.

2. The device according to claim 1, wherein the perforations have a maximum distance to the front end of the shell that is equal to approximately the length of the hollow cylinder/3.

3. The device according to claim 1, wherein a diameter of each perforation ranges between 0.9 mm to 3.3 mm.

4. The device according to claim 1, wherein the shell defines an inner diameter and an opposed outer diameter, such that a ratio between the outer diameter of the hollow cylinder measured in mm and a total outlet area of the perforations measured in mm$^2$ ranges between 0.19 and 0.36 mm$^{-1}$.

5. A device for cement augmentation of bone implants, the device comprising:
  a shell defining a closed front end configured to be inserted into bone and capable of blocking material from passing therethrough, an opposed open rear end that is spaced from the front end along a first direction and includes an inner surface defining a hole, and a shell portion that extends between the rear end and the front end and defines an inner cavity that is in communication with the hole, the shell further defining a plurality of perforations that extend through the shell portion in communication with the inner cavity, the shell having a shell length measured from the front end to the rear end along the first direction and the perforations each having a central axis whereby each central axis is located between the front end and a midline of the shell length; and
  a bone implant having a length so as to define a proximal end and an opposed distal end, the bone implant having an exterior thread that extends from the distal end toward the proximal end along a portion of the length such that the exterior thread of the bone implant mates with the inner surface of the shell to thereby advance the portion of the bone implant having the exterior thread into the inner cavity of the shell as the bone implant is rotated with respect to the shell;
  wherein (i) the shell receives unhardened bone cement in the inner cavity, and (ii) the length of the bone implant is sufficient to extend within a majority of the inner cavity such that the distal end of the bone implant presses against the bone cement as the bone implant advances into the shell, and the perforations are sized such that the pressed bone cement is driven through the perforations, wherein the shell is filled at least partially with unhardened bone cement.

6. The device according to claim 5, wherein the shell and the bone implant have complementary shapes.

7. The device according to claim 5, wherein the rear end of the shell is configured as a coupling for connection to a bone cement syringe.

8. The device according to claim 7, wherein the rear end of the shell is configured as a plug-in connection for coupling with a bone cement syringe.

9. The device according to claim 5, wherein the inner surface of the shell defines an interior thread configured to engage the exterior thread of the implant.

10. The device according to claim 9, wherein the interior thread is formed proximate to the hole.

11. The device according to claim 5, wherein a cross-section of the hole of the shell and a cross-section of the bone implant define a common shape.

12. The device according to claim 5, wherein the central axes of the perforations are located between the front end of the shell and the shell length/3.

13. The device according to claim 5, wherein a diameter of each perforation ranges between 0.9 mm to 3.3 mm.

14. The device according to claim 5, wherein a wall thickness of the shell ranges between approximately 0.1 mm to 2.0 mm.

15. The device according to claim 5, wherein the perforations are in the form of a mesh grid.

16. The device according to claim 5, wherein the bone implant is selected from the group consisting of bone screws, blades, spiral blades and bone nails.

17. The device according to claim 5, wherein the closed front end is devoid of the perforations.

18. A device for cement augmentation of bone implants, the device comprising:
a shell defining a closed front end configured to be inserted into bone and capable of blocking material from passing therethrough, an opposed open rear end that is spaced from the front end along a first direction and includes an inner surface defining a hole, and a shell portion that extends between the rear end and the front end and defines an inner cavity that is in communication with the hole, the shell further defining a plurality of perforations that extend through the shell portion in communication with the inner cavity, the shell having a shell length measured from the front end to the rear end along the first direction and the perforations each having a central axis whereby each central axis is located between the front end and a midline of the shell length; and
a bone implant having a length so as to define a proximal end and an opposed distal end, the bone implant having an exterior thread that extends from the distal end toward the proximal end along a portion of the length such that the exterior thread of the bone implant mates with the inner surface of the shell to thereby advance the portion of the bone implant having the exterior thread into the inner cavity of the shell as the bone implant is rotated with respect to the shell;
wherein (i) the shell receives unhardened bone cement in the inner cavity, and (ii) the length of the bone implant is sufficient to extend within a majority of the inner cavity such that the distal end of the bone implant presses against the bone cement as the bone implant advances into the shell, and the perforations are sized such that the pressed bone cement is driven through the perforations, wherein a diameter of the at least one perforation ranges between approximately 1.5 mm to approximately 2.5 mm.

19. A device for cement augmentation of bone implants, the device comprising:
a shell defining a closed front end configured to be inserted into bone and capable of blocking material from passing therethrough, an opposed open rear end that is spaced from the front end along a first direction and includes an inner surface defining a hole, and a shell portion that extends between the rear end and the front end and defines an inner cavity that is in communication with the hole, the shell further defining a plurality of perforations that extend through the shell portion in communication with the inner cavity, the shell having a shell length measured from the front end to the rear end along the first direction and the perforations each having a central axis whereby each central axis is located between the front end and a midline of the shell length; and
a bone implant having a length so as to define a proximal end and an opposed distal end, the bone implant having an exterior thread that extends from the distal end toward the proximal end along a portion of the length such that the exterior thread of the bone implant mates with the inner surface of the shell to thereby advance the portion of the bone implant having the exterior thread into the inner cavity of the shell as the bone implant is rotated with respect to the shell;
wherein (i) the shell receives unhardened bone cement in the inner cavity, and (ii) the length of the bone implant is sufficient to extend within a majority of the inner cavity such that the distal end of the bone implant presses against the bone cement as the bone implant advances into the shell, and the perforations are sized such that the pressed bone cement is driven through the perforations, wherein the number of perforations is at least 20.

20. A device for cement augmentation of bone implants, the device comprising:
a shell defining a closed front end configured to be inserted into bone and capable of blocking material from passing therethrough, an opposed open rear end that is spaced from the front end along a first direction and includes an inner surface defining a hole, and a shell portion that extends between the rear end and the front end and defines an inner cavity that is in communication with the hole, the shell further defining a plurality of perforations that extend through the shell portion in communication with the inner cavity, the shell having a shell length measured from the front end to the rear end along the first direction and the perforations each having a central axis whereby each central axis is located between the front end and a midline of the shell length; and
a bone implant having a length so as to define a proximal end and an opposed distal end, the bone implant having an exterior thread that extends from the distal end toward the proximal end along a portion of the length such that the exterior thread of the bone implant mates with the inner surface of the shell to thereby advance the portion of the bone implant having the exterior thread into the inner cavity of the shell as the bone implant is rotated with respect to the shell;
wherein (i) the shell receives unhardened bone cement in the inner cavity, and (ii) the length of the bone implant is sufficient to extend within a majority of the inner cavity such that the distal end of the bone implant presses against the bone cement as the bone implant advances into the shell, and the perforations are sized such that the pressed bone cement is driven through the perforations, wherein the number of perforations is at least 40.

21. A device for cement augmentation of bone implants, the device comprising:
a shell defining a closed front end configured to be inserted into bone and capable of blocking material from passing therethrough, an opposed open rear end that is spaced from the front end along a first direction and includes an inner surface defining a hole, and a shell portion that extends between the rear end and the front end and defines an inner cavity that is in communication with the hole, the shell further defining a plurality of perforations that extend through the shell portion in communication with the inner cavity, the shell having a shell length measured from the front end to the rear end along the first direction and the perforations each having a central axis whereby each central axis is located between the front end and a midline of the shell length; and a bone implant having a length so as to define a proximal end and an opposed distal end, the bone implant having an exterior thread that extends from the distal end toward the proximal end along a portion of the length such that the exterior thread of the bone implant mates with the inner surface of the shell to thereby advance the portion of the bone implant having the exterior thread into the inner cavity of the shell as the bone implant is rotated with respect to the shell;

wherein (i) the shell receives unhardened bone cement in the inner cavity, and (ii) the length of the bone implant is sufficient to extend within a majority of the inner cavity such that the distal end of the bone implant presses against the bone cement as the bone implant advances into the shell, and the perforations are sized such that the pressed bone cement is driven through the perforations, wherein the shell defines an inner diameter and an opposed outer diameter, such that a ratio between the outer diameter of the shell measured in mm and a total outlet area of the perforations measure in $mm^2$ ranges between 0.19 and 0.36 $mm^{-1}$.

* * * * *